United States Patent
Lee et al.

(10) Patent No.: US 9,970,906 B2
(45) Date of Patent: May 15, 2018

(54) APPARATUS FOR ANALYZING ACTIVE MATERIAL OF SECONDARY BATTERY AND METHOD OF ANALYZING ACTIVE MATERIAL USING THE SAME

(71) Applicant: Samsung Electronics Co., Ltd., Suwon-si, Gyeonggi-do (KR)

(72) Inventors: Jooho Lee, Hwaseong-si (KR); Changseung Lee, Yongin-si (KR); Jeoyoung Shim, Yongin-si (KR); Sunghee Lee, Suwon-si (KR); Woosung Jeon, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 237 days.

(21) Appl. No.: 14/734,229

(22) Filed: Jun. 9, 2015

(65) Prior Publication Data
US 2016/0054267 A1  Feb. 25, 2016

(30) Foreign Application Priority Data

Aug. 21, 2014  (KR) .................. 10-2014-0109046

(51) Int. Cl.
*G01N 29/12* (2006.01)
*G01N 29/24* (2006.01)

(52) U.S. Cl.
CPC ......... *G01N 29/12* (2013.01); *G01N 29/2437* (2013.01); *G01N 2291/0256* (2013.01); *G01N 2291/2697* (2013.01)

(58) Field of Classification Search
CPC .... G01N 29/12; G01N 29/2437; G01N 27/27; G01N 27/4161
See application file for complete search history.

(56) References Cited

U.S. PATENT DOCUMENTS

| 8,173,436 B2 | 5/2012 | Zhang et al. | |
|---|---|---|---|
| 2010/0134210 A1* | 6/2010 | Umeda | H03H 3/04 333/189 |
| 2011/0223620 A1* | 9/2011 | Koyama | G01N 5/02 435/7.31 |

FOREIGN PATENT DOCUMENTS

| JP | 2009123448 A | 6/2009 |
|---|---|---|
| JP | 2013137249 A | 7/2013 |
| KR | 20140059400 A | 5/2014 |

OTHER PUBLICATIONS

Kaoru Dokko et al., "Highrate discharge capability of single particle elctrode of $LiCoO_2$", Journal of Power Sources 189, 2008 Elsevier B.V., pp. 783-785.

(Continued)

*Primary Examiner* — Paul West
(74) *Attorney, Agent, or Firm* — Harness, Dickey & Pierce, P.L.C.

(57) ABSTRACT

An apparatus for analyzing an active material of a secondary battery may include: a first electrode; a piezoelectric layer on the first electrode; a second electrode on the piezoelectric layer, configured to provide a voltage having a polarity opposite to a polarity of the first electrode; and/or an insulating layer on the second electrode and including a through hole exposing a portion of the second electrode. A method of analyzing an active material of a secondary battery may include: disposing an active material in a through hole of a bulk acoustic resonator, in which a first electrode, a piezoelectric layer, a second electrode, and an insulating layer are stacked; measuring a resonance frequency of the resonator by applying an electric signal to the first and second electrodes of the resonator; and/or measuring a weight of the active material in the through hole, based on the measured resonance frequency.

13 Claims, 9 Drawing Sheets (56) References Cited

OTHER PUBLICATIONS

Humberto Campanella et al., "Localized-mass detection based on thin-film bulk acoustic wave resonators (FBAR): Area and mass location aspects", ScienceDirect Sensors and Actuators, 2007 Elsevier B.V., pp. 322-328.

Humberto Campanella et al., "Localized and distributed mass detectors with high sensitivity based on thin-film bulk acoustic resonators", Applied Physics Letters 89, 2006, AIP Publishing, pp. 1-4.

Bong-Seok Kim et al., "Fabrication of $Li_2CO_3$-doped Zno Thin Film Bulk Acoustic Resonator and Structural, Electrical Properties as a Function of Annealing Temperatures", Journal of the Korean Institute of Electrical and Electronic Material Engineers, Feb. 2007, vol. 20, No. 2, pp. 152-155.

* cited by examiner

APPARATUS FOR ANALYZING ACTIVE MATERIAL OF SECONDARY BATTERY AND METHOD OF ANALYZING ACTIVE MATERIAL USING THE SAME

CROSS-REFERENCE TO RELATED APPLICATION(S)

This application claims priority from Korean Patent Application No. 10-2014-0109046, filed on Aug. 21, 2014, in the Korean Intellectual Property Office (KIPO), the entire contents of which are incorporated herein by reference.

BACKGROUND

1. Field

Some example embodiments may relate generally to apparatuses for analyzing active materials of secondary batteries. Some example embodiments may relate generally to methods of analyzing the active materials using the same. Some example embodiments may relate generally to apparatuses for precisely analyzing properties of active materials used in secondary batteries. Some example embodiments may relate generally to methods of analyzing the active materials using the same.

2. Description of Related Art

Secondary batteries, which may have a high applicability to products and have electrical characteristics, such as high energy density, may not only be used in portable devices, but also may be commonly used in electric vehicles (EVs) driven by an electric driving source, or by hybrid vehicles (HVs).

Particularly, secondary batteries which are loaded in the EVs or the HVs may be high capacity batteries. To realize the high capacity secondary batteries, excellent performance, price, and stability of the secondary batteries may be demanded. However, current materials forming the secondary batteries may not be able to meet such a demand. Accordingly, there may have been active efforts to develop materials forming the secondary batteries.

However, currently, there may be no appropriate devices to analyze or evaluate properties of the materials of the secondary batteries. As a result, development of the materials forming the secondary batteries may be being delayed. Therefore, it is required to develop methods and apparatuses for analyzing or evaluating the properties of the materials of the secondary batteries and properties of the secondary batteries themselves.

SUMMARY

Some example embodiments may provide apparatuses for analyzing n active materials of secondary batteries.

The apparatuses may precisely measure weights of the active materials used in the secondary batteries.

The apparatuses may precisely measure electrical and chemical properties of the active materials.

Some example embodiments may provide methods of analyzing active materials of secondary batteries using the apparatuses.

In some example embodiments, an apparatus for analyzing an active material of a secondary battery may comprise: a first electrode; a piezoelectric layer on the first electrode; a second electrode on the piezoelectric layer, configured to provide a voltage having a polarity opposite to a polarity of the first electrode; and/or an insulating layer on the second electrode and comprising a first through hole exposing a portion of the second electrode.

In some example embodiments, a first active material is injected in the first through hole. A weight of the first active material accommodated in the first through hole may be detected based on a resonance frequency generated in the piezoelectric layer.

In some example embodiments, the insulating layer may further comprise a second through hole that does not overlap the second electrode and is spaced apart from the first through hole.

In some example embodiments, the apparatus may further comprise: a third electrode apart from the second electrode. The second through hole may expose a portion of the third electrode.

In some example embodiments, a second active material, having a different charge and discharge potential from the first active material, may be injected in the second through hole.

In some example embodiments, a chamber layer, which encloses the first and second through holes and in which an electrolyte is accommodated, may be above the insulating layer.

In some example embodiments, the apparatus may further comprise: a substrate below the first electrode.

In some example embodiments, the substrate may comprise a cavity in at least a portion of a region of the substrate. The region may overlap the first electrode.

In some example embodiments, the substrate may comprise a reflective layer in at least a portion of a region of the substrate. The region may overlap the first electrode.

In some example embodiments, a method of analyzing an active material of a secondary battery may comprise: disposing a first active material in a first through hole of a bulk acoustic resonator, in which a first electrode, a piezoelectric layer, a second electrode, and an insulating layer are sequentially stacked, wherein the first through hole is in the insulating layer to expose a portion of the second electrode; measuring a resonance frequency of the bulk acoustic resonator by applying an electric signal to the first and second electrodes of the bulk acoustic resonator; and/or measuring a weight of the first active material in the first through hole, based on the measured resonance frequency.

In some example embodiments, the method may further comprise: disposing a second active material apart from the first active material; and/or disposing an electrolyte to contact the first and second active materials.

In some example embodiments, the method may further comprise: detecting electrical and chemical properties of the first active material per unit weight.

In some example embodiments, the second active material may have a different charge and discharge potential from the first active material.

In some example embodiments, the first active material may be a positive active material or a negative active material.

In some example embodiments, the method may further comprise: generating an ultrasound wave by applying an electric signal to the first and second electrodes; and/or detecting a bonding property between the second electrode and the first active material by using the generated ultrasound wave.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

Figure 1:
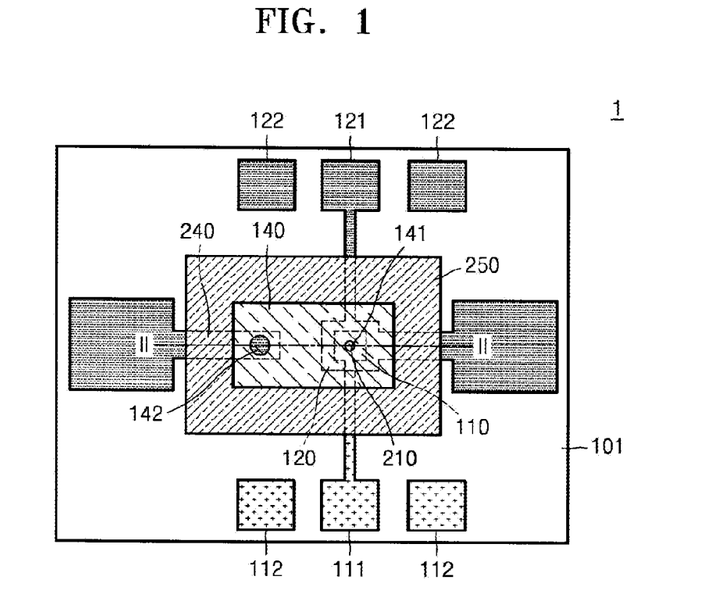
FIG. 1 is a plan view of an apparatus for analyzing an active material of a secondary battery according to some example embodiments.
Figure 2:
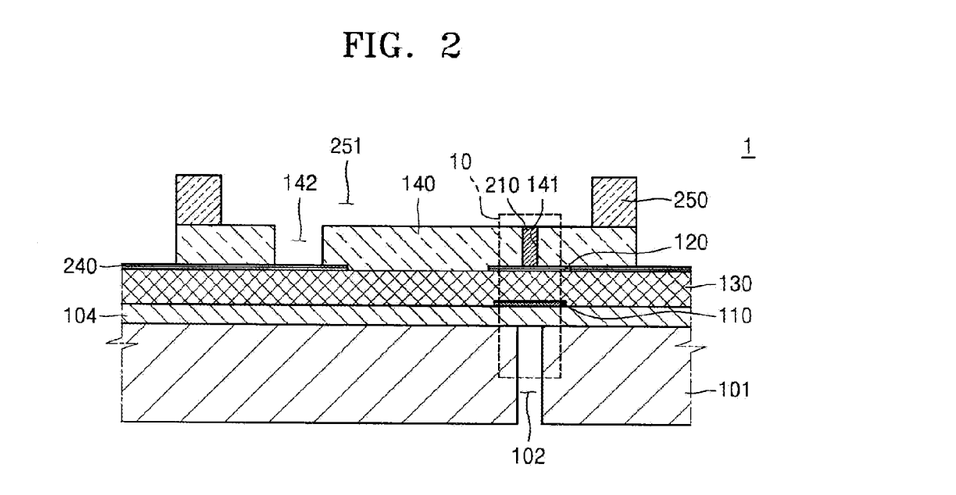
FIG. 2 is a cross-sectional view taken along a line II-II of FIG. 1.

FIG. 1 is a plan view of an apparatus for analyzing an active material of a secondary battery 1 according to some example embodiments. FIG. 2 is a cross-sectional view taken along a line II-II of FIG. 1.

Referring to FIG. 1, the apparatus for analyzing the active material of the secondary battery 1 includes a substrate 101, a first electrode 110, a piezoelectric layer 130, a second electrode 120, and an insulating layer 140.

The first electrode 110 may be formed on the substrate 101. A cavity 102 may be formed in at least a portion of a region of the substrate 101, the region overlapping the first electrode 110.

The substrate 101 may be a silicon substrate. However, materials of the substrate 101 are not limited thereto and may vary. An insulating thin film 104 may be formed between the substrate 101 and the first electrode 110. The insulating thin film 104 may include, for example, silicon oxide.

The first electrode 110 may be a metal layer. The first electrode 110 may include any one selected from the metal materials consisting of molybdenum (Mo), gold (Au), copper (Cu), (palladium) Pd, nickel (Ni), titanium (Ti), chromium (Cr), iron (Fe), cobalt (Co), platinum (Pt), and ruthenium (Ru), or any mixture thereof. The first electrode 110 may be formed on the substrate 101 by a metal patterning method, such as etching and a lift-off method. The first electrode 110 may be formed to have a thickness of about 10 nanometers (nm) to about 1,000 nm.

A first electrode pad 111 is formed at an end of the first electrode 110. Ground pads 112 may be disposed at two sides of the first electrode pad 111. A ground voltage may be applied to the ground pads 112.

The piezoelectric layer 130 may be formed on the first electrode 110 and be a thin film having a piezoelectric property. The piezoelectric layer 130 may include any one of aluminum nitride (AlN), ZnO, and lead zirconate titanate (PZT), or any mixture thereof. The piezoelectric layer 130 may be formed to have a thickness of about 10 nm to about 3,000 nm.

The second electrode 120 is formed on the piezoelectric layer 130 and may provide a voltage of a polarity opposite to a polarity of the first electrode 110. The second electrode 120 may be a metal layer. The second electrode 120 may include any one selected from the metal materials consisting of Mo, Au, Cu, Pd, Ni, Ti, Cr, Fe, Co, Pt, and Ru, and any mixtures thereof. The second electrode 120 may be formed on the substrate 101 by a metal patterning method, such as etching and a lift-off method. The second electrode 120 may be formed to have a thickness of about 10 nm to about 1,000 nm.

A second electrode pad 121 is formed at an end of the second electrode 120. Ground pads 122 may be disposed at two sides of the second electrode pad 121. A ground voltage may be applied to the ground pads 122.

At least a portion of the insulating layer 140 is formed on the second electrode 120. The insulating layer 140 may be formed by using various methods, such as atomic layer deposition (ALD), chemical vapor deposition (CVD), and evaporation.

The insulating layer 140 includes a first through hole 141 exposing at least a portion of the second electrode 120. The first through hole 141 may be formed by selectively removing the insulating layer 140 by etching.

The first electrode 110, the piezoelectric layer 130, the second electrode 120, and the insulating layer 140 which are described above may function as a bulk acoustic resonator 10. In other words, at least some of the first electrode 110, the piezoelectric layer 130, the second electrode 120, and the insulating layer 140 may form the bulk acoustic resonator 10.

Sound waves are generated in the piezoelectric layer 130, when an electric signal, for example, an alternating voltage, is applied to the first and second electrodes 110 and 120 of the bulk acoustic resonator 10. The sound waves are reflected in the first and second electrodes 110 and 120 and have a desired resonance frequency (that may or may not be predetermined). The resonance frequency of the bulk acoustic resonator 10 may vary according to voltage applied, temperature, or weight.

The first through hole 141 may accommodate a first active material 210. The resonance frequency of the bulk acoustic resonator 10 before the first active material 210 is injected (or disposed) in the first through hole 141 and the resonance frequency of the bulk acoustic resonator 10 after the first active material 210 is injected in the first through hole 141 are measured. A weight of the first active material 210 injected in the first through hole 141 may be detected based on a change in the resonance frequency, before and after the first active material 210 is injected in the first through hole 141.

Figure 3A:
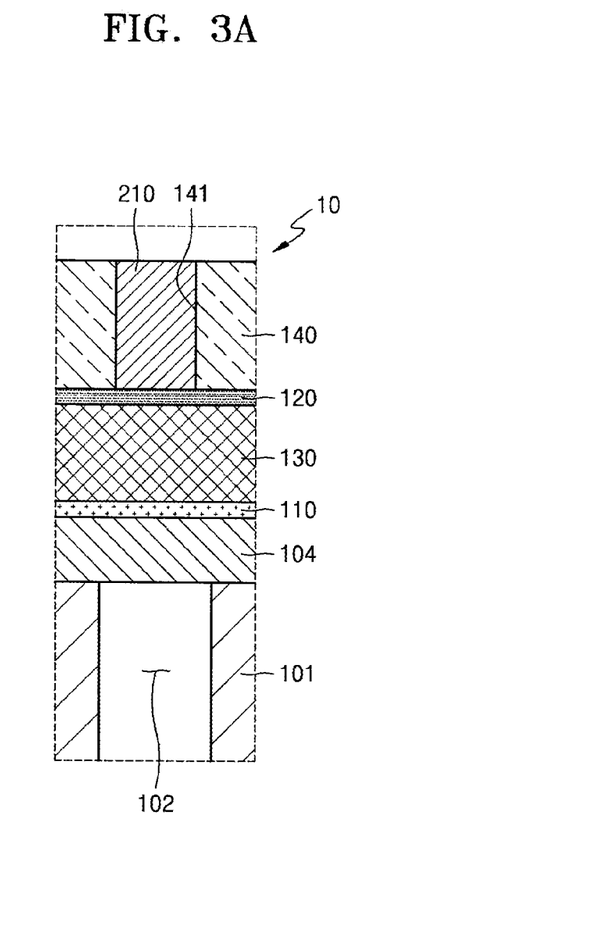
FIG. 3A is an enlarged view of a bulk acoustic resonator of FIG. 2.
Figure 3B:
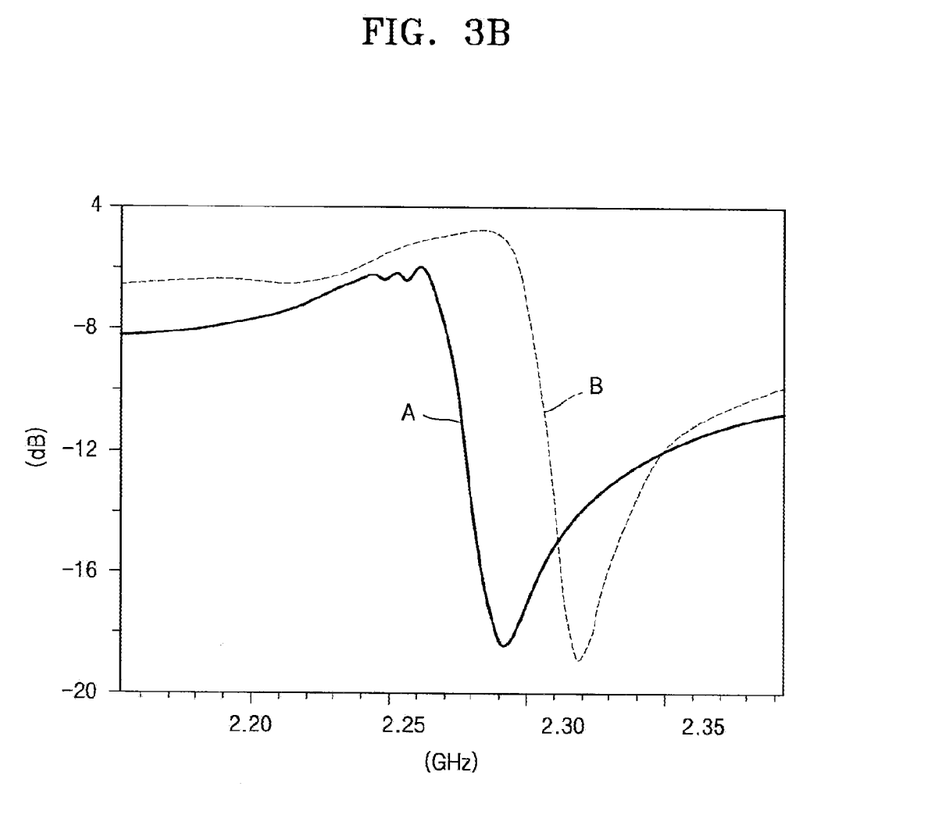
FIG. 3B is a view illustrating a measurement of a resonance frequency of the bulk acoustic resonator of FIG. 2.

FIG. 3A is an enlarged view of the bulk acoustic resonator 10 of FIG. 2. FIG. 3B is a view illustrating a measurement of the resonance frequency of the bulk acoustic resonator 10 of FIG. 2. FIG. 3B illustrates resonance properties before and after the first active material 210 is injected in the first through hole 141.

Referring to FIGS. 3A and 3B, before the first active material 210 is injected in the first through hole 141, the bulk acoustic resonator 10 has a resonance property such as A. After the first active material 210 is injected in the first through hole 141, the bulk acoustic resonator 10 has a resonance property such as B. When comparing A and B, it is understood that the resonance frequencies differ from each other. That is, according to whether the first active material 210 is injected in the first through hole 141 or not, the resonance frequencies differ.

The bulk acoustic resonator 10 has the characteristic that the resonance frequency thereof varies according to the weight. By using such a characteristic of the bulk acoustic resonator 10, the weight of the first active material 210 may be measured based on the difference of the resonance frequencies.

Referring again to FIG. 2, the apparatus for analyzing the active material of the secondary battery 1 according to some example embodiments may further include a second through hole 142, which does not overlap the second electrode 120 and is spaced apart from the first through hole 141, and an electrolyte accommodation unit 251 for accommodating an electrolyte 230.

A second active material 220 which has a different charge and discharge potential from the first active material 210 may be accommodated in the second through hole 142.

The second through hole 142 may be formed on the insulating layer 140 to be apart from the first through hole 141. Since the second through hole 142 is spaced apart from the first through hole 141, the first active material 210 injected in the first through hole 141 and the second active material 220 injected in the second through hole 142 may be apart from each other.

A third electrode 240 which is apart from the second electrode 120 may be disposed below the second through hole 142. Accordingly, when the second active material 220 is injected in the second through hole 142, the second active material 220 may contact the third electrode 240.

The third electrode 240 may be a metal layer. The third electrode 240 may include any one selected from the metal materials consisting of Mo, Au, Cu, Pd, Ni, Ti, Cr, Fe, Co, Pt, and Ru, or any mixture thereof. The third electrode 240 may be formed together with the second electrode 120, when the second electrode 120 is formed.

The electrolyte accommodation unit 251 may be formed above the first through hole 141 and the second through hole 142. A chamber layer 250 for defining the electrolyte accommodation unit 251 may be formed on the insulating layer 140. When the electrolyte 230 is a liquid electrolyte, the chamber layer 250 may be formed continuously to accommodate the liquid electrolyte, as illustrated in FIG. 1. However, when the electrolyte 230 is a solid electrolyte, the chamber layer 250 does not necessarily need to be continuously formed, and may be discontinuously formed.

Materials of the chamber layer 250 may be the same as materials of the insulating layer 140. However, the materials of the chamber layer 250 are not limited thereto and may include any material which does not react with the electrolyte 230.

Figure 4:
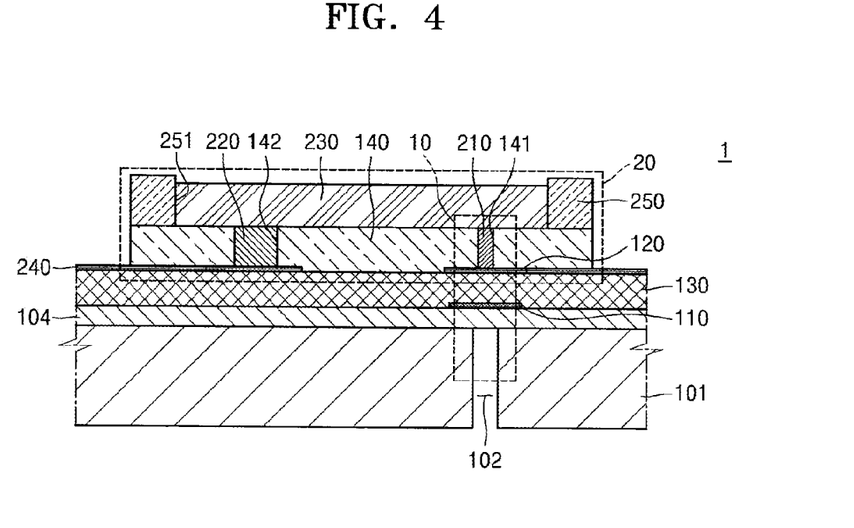
FIG. 4 illustrates an example of a state in which first and second active materials and an electrolyte are injected in first and second through holes and an electrolyte accommodation unit, in the apparatus for analyzing the active material of the secondary battery of FIG. 2.

FIG. 4 illustrates a state in which the first and second active materials 210 and 220 and the electrolyte 230 are injected in the first and second through holes 141 and 142 and the electrolyte accommodation unit 251 in the apparatus for analyzing the active material of the secondary battery 1 of FIG. 2.

Referring to FIG. 4, in addition to the first active material 210, the weight of which is measured, the second active material 220 is injected in the second through hole 142, and the electrolyte 230 is injected in the electrolyte accommodation unit 251. The electrolyte 230 injected in the electrolyte accommodation unit 251 contacts the first and second active materials 210 and 220. Accordingly, a battery environment 20 in which charging and discharging may occur may be formed.

Here, the second electrode 120 may function as a first current collector in the battery environment 20. That is, the second electrode 120 may not only function as an electrode in the bulk acoustic resonator 10, but may also function as the current collector in the battery environment 20. The third electrode 240 may function as a second current collector in the battery environment 20.

In this state, an electrical and chemical experiment is conducted via the second electrode 120 and the third electrode 240. Through the electrical and chemical experiment, electrical and chemical properties of the first active material 210 per unit weight may be detected. Methods of detecting the electrical and chemical properties may include any kind which is used by one of ordinary skill in the art.

The electrical and chemical property may include, for example, discharge capacity, life span, initial efficiency, a high rate charge and discharge property, and a low rate charge and discharge property. However, the electrical and chemical properties are not limited thereto, and may include any such property which may be measured in the battery environment 20.

Also, when a volume of the first active material 210 is known, a density of the first active material 210 may be detected. Measuring the volume of the first active material 210 is generally easier than measuring the weight of the first active material 210. For example, the volume of the first active material 210 may be measured by analysis using an optical apparatus and may be also measured by a volume of the first through hole 141. In addition to these, various volume measuring methods may be used to measure the volume of the first active material 210. The electrical and chemical property of the first active material 210 per density may be detected, based on the bulk and the weight of the first active material 210.

The first active material 210 may be a positive active material. Any kind of positive active material which is used in the related art by one of ordinary skill in the art may be used. For example, the positive active material may be a compound represented by any one of the formulas consisting of $Li_aA_{1-b}R_bD_2$ (here, $0.90 \le a \le 1$, and $0 \le b \le 0.5$); $Li_aE_{1-b}R_bO_{2-c}D_c$ (here, $0.90 \le a \le 1$, $0 \le b \le 0.5$, $0 \le c \le 0.05$); $LiE_{2-b}R_bO_{4-c}D_c$ (here, $0 \le b \le 0.5$, $0 \le c \le 0.05$); $Li_aNi_{1-b-c}Co_bR_cD_\alpha$ (here, $0.90 \le a \le 1$, $0 \le b \le 0.5$, $0 \le c \le 0.05$, $0 \le \alpha \le 2$); $Li_aNi_{1-b-c}Co_bR_cO_{2-\alpha}T_\alpha$ (here, $0.90 \le a \le 1$, $0 \le b \le 0.5$, $0 \le c \le 0.05$, $0 \le \alpha \le 2$); $Li_aNi_{1-b-c}Co_bR_cO_{2-\alpha}T_2$ (here, $0.90 \le a \le 1$, $0 \le b \le 0.5$, $0 \le c \le 0.05$, $0 \le \alpha \le 2$); $Li_aNi_{1-b-c}Mn_bR_cD_\alpha$ (here, $0.90 \le a \le 1$, $0 \le b \le 0.5$, $0 \le c \le 0.05$, $0 \le \alpha \le 2$); $Li_aNi_{1-b-c}Mn_bR_cO_{2-\alpha}T_\alpha$ (here, $0.90 \le a \le 1$, $0 \le b \le 0.5$, $0 \le c \le 0.05$, $0 \le \alpha \le 2$); $Li_aNi_{1-b-c}Mn_bR_cO_{2-\alpha}T_2$ (here, $0.90 \le a \le 1$, $0 \le b \le 0.5$, $0 \le c \le 0.05$, $0 \le \alpha \le 2$); $Li_aNi_bE_cG_dO_2$ (here, $0.90 \le a \le 1$, $0 \le b \le 0.9$, $0 \le c \le 0.5$, $0.001 \le d \le 0.1$); $Li_aNi_bCo_cMn_dGeO_2$ (here, $0.90 \le a \le 1$, $0 \le b \le 0.9$, $0 \le c \le 0.5$, $0 \le d \le 0.5$, $0.001 \le e \le 0.1$); $Li_aNiG_bO_2$ (here, $0.90 \le a \le 1$, $0.001 \le b \le 0.1$); $Li_aCoG_bO_2$ (here, $0.90 \le a \le 1$, $0.001 \le b \le 0.1$); $Li_aMnG_bO_2$ (here, $0.90 \le a \le 1$, $0.001 \le b \le 0.1$); $Li_aMn_2G_bO_4$ (here, $0.90 \le a \le 1$, $0.001 \le b \le 0.1$); $QO_2$; $QS_2$; $LiQS_2$; $V_2O_5$; $LiV_2O_5$; $LiZO_2$; $LiNiVO_4$; $Li_{(3-f)}J_2(PO_4)_3$ (here, $0 \le f \le 2$); $Li_{(3-f)}Fe_2(PO_4)_3$ (here, $0 \le f \le 2$); and $LiFePO_4$.

In the above formulas, Ge is germanium, Li is lithium, A is Ni, Co, manganese (Mn), or a mixture thereof; R is aluminum (Al), Ni, Co, Mn, Cr, Fe, magnesium (Mg), strontium (Sr), vanadium (V), a rare earth element, or a mixture thereof; D is oxygen (O), fluorine (F), sulfur (S), phosphorous (P), or a mixture thereof; E is Co, Mn, or a mixture thereof; T is F, S, P, or a mixture thereof; G is Al, Cr, Mn, Fe, Mg, lanthanum (La), cerium (Ce), Sr, V, or a mixture thereof; Q is Ti, Mo, Mn, or a mixture thereof; Z is Cr, V, Fe, scandium (Sc), yttrium (Y), or a mixture thereof; and J is V, Cr, Mn, Co, Ni, Cu, or a mixture thereof.

Of course, a compound having a coating layer on a surface the above compound may be used, or a mixture of the above compound and the compound having the coating layer may be used. The coating layer may include a coating element compound, such as coating element oxide, hydroxide, coating element oxyhydroxide, coating element oxycarbonate, or coating element hydroxycarbonate. The coating element compound included in the coating layer may be amorphous or crystalline. The coating element included in the coating layer may be Mg, Al, Co, potassium (K), sodium (Na), calcium (Ca), silicon (Si), Ti, V, tin (Sn), Ge, gallium (Ga), boron (B), arsenic (As), zirconium (Zr), or a mixture thereof. A process of forming the coating layer may be performed by any coating method (for example, a spray coating method or an immersion method) which does not adversely affect the property of the positive active material when using the above-described coating elements in the above-described compounds. This aspect is well-known to one of ordinary skill in the art and, thus, will not be described in detail.

The first active material 210 may be, for example, lithium salt, such as lithium cobalt oxide (hereinafter, referred to as LCO), lithium nickel oxide, lithium nickel cobalt oxide, lithium nickel cobalt aluminum oxide (hereinafter, referred to as NCA), lithium nickel cobalt manganese oxide (hereinafter, referred to as NCM), lithium manganese oxide, lithium iron phosphate, nickel sulfide, copper sulfide, sulfur, iron oxide, or vanadium oxide. These may be used singularly or as a mixture of two or more kinds, as the first active material 210.

The second active material 220 may be a negative active material. The negative active material may include any material which may be used as the negative active material of the secondary battery by one of ordinary skill in the art. The negative active material may be, for example, at least one selected from the group consisting of a lithium metal, a metal which may be alloyed with lithium, transition metal oxide, non-transition metal oxide, a material which may dope and dedope lithium, and a carbon-based material. In some example embodiments, a lithium secondary battery is exemplified as the secondary battery. However, the secondary battery is not limited thereto, and may be another secondary battery, for example, a magnesium secondary battery.

The metal which may be alloyed with lithium may be, for example, Si, Sn, Al, indium (In), Ge, lead (Pb), bismuth (Bi), antimony (Sb), an Si—X alloy (where X is an alkali metal, an alkali earth metal, a group 13 element, a group 14 element, a transition metal, a rare earth element, or a mixture element thereof, and Si is not), and an Sn—X alloy (where X is an alkali metal, an alkali earth metal, a group 13 element, a group 14 element, a transition metal, a rare earth element, or a mixture element thereof, and Sn is not). The element X may be Mg, Ca, Sr, barium (Ba), radium (Ra), Sc, Y, Ti, Zr, hafnium (Hf), rutherfordium (Rf), V, niobium (Nb), tantalum (Ta), dubnium (Db), Cr, Mo, tungsten (W), seaborgium (Sg), technetium (Tc), rhenium (Re), bohrium (Bh), Fe, Pb, Ru, osmium (Os), hassium (Hs), rhodium (Rh), iridium (Ir), Pd, Pt, Cu, silver (Ag), Au, zinc (Zn), cadmium (Cd), B, Al, Ga, Sn, In, Ti, Ge, P, As, Sb, Bi, S, selenium (Se), tellurium (Te), polonium (Po), or a mixture thereof.

The transition metal oxide may be, for example, tungsten oxide, molybdenum oxide, titanium oxide, lithium titanium oxide, vanadium oxide, or lithium vanadium oxide.

The non-transition metal oxide may be, for example, $SnO_2$ or $SiO_x$ ($0<x<2$).

The material which may dope and dedope lithium may be, for example, Sn, $SnO_2$, an Sn—X alloy (where X is an alkali metal, an alkali earth metal, a group 11 element, a group 12 element, a group 13 element, a group 14 element, a group 15 element, a group 16 element, a transition metal, a rare earth element, or a mixture element thereof, and Sn is not). The element X may be Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Ti, Ge, P, As, Sb, Bi, S, Se, Te, Po, or a mixture thereof.

The carbon-based material may be crystalline carbon, amorphous carbon, or a mixture thereof. The carbon-based material may include natural graphite, synthetic graphite, graphite carbon fiber, resin plasticity carbon, pyrolysis vapor growth carbon, coke, mesocarbon microbeads (MCMB), furfuryl alcohol resin plasticity carbon, polyacene, pitch-based carbon fiber, vapor growth carbon fiber, soft carbon (low temperature plasticity carbon) or hard carbon, or mesophase pitch carbide. Such a material is the negative active material and may be used singularly or as a mixture of two or more kinds.

The carbon-based material may be amorphous, flat, flake, spherical, fibrous, or a mixture thereof.

The electrolyte 230 may be a liquid electrolyte, an organic solid electrolyte, or an inorganic solid electrolyte. The electrolyte 230 may be any kind of liquid electrolyte, organic solid electrolyte, or inorganic solid electrolyte which may be used by one of ordinary skill in the art.

The liquid electrolyte may include a non-aqueous solvent and lithium salt. The non-aqueous solvent may be a carbonate, ester, ether, ketone, amine, or phosphine-based solvent. The lithium salt is a material which is easily dissolved in the non-aqueous solvent. The lithium salt may be, for example, at least one of LiCl, LiBr, LiI, $LiClO_4$, $LiBF_4$, $LiB_{10}Cl_{10}$, $LiPF_6$, $LiCF_3SO_3$, $LiCF_3CO_2$, $LiAsF_6$, $LiSbF_6$, $LiAlCl_4$, $CH_3SO_3Li$, $CF_3SO_3Li$, $(CF_3SO_2)_2NLi$, lithium chloroborate, lower aliphatic carbonic acid lithium, 4-phenyl boric acid lithium, and imide. In the above formulas, Br is bromine, C is carbon, Cl is chlorine, H is hydrogen, I is iodine, and N is nitrogen.

The organic solid electrolyte may be, for example, a polymer, such as polyethylene derivatives, polyethylene oxide derivatives, polypropylene oxide derivatives, a phosphate ester polymer, poly agitation lysine, polyester sulfide, polyvinyl alcohol, poly fluoride vinylidene, or a dissociable group.

The inorganic solid electrolyte may be, for example, lithium nitride, such as $Li_3N$, LiI, $Li_5NI_2$, $Li_3N$—LiI—LiOH, $LiSiO_4$, $LiSiO_4$—LiI—LiOH, $Li_2SiS_3$, $Li_4SiO_4$, $Li_4SiO_4$—LiI—LiOH, $Li_3PO_4$—$Li_2S$—$SiS_2$, and LiPON, a halide, or a sulfate.

Figure 5:
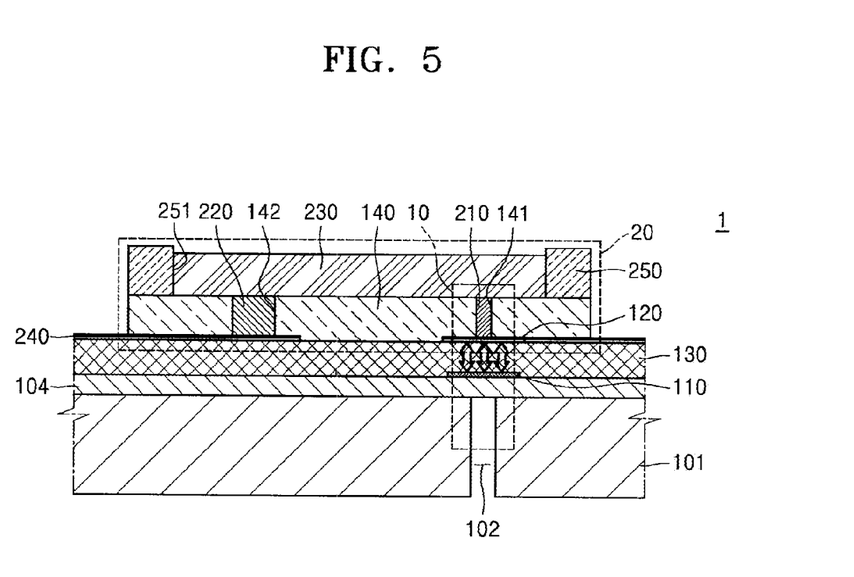
FIG. 5 illustrates a state in which electric power is supplied in first and second electrodes in the apparatus for analyzing the active material of the secondary battery of FIG. 4.

FIG. 5 illustrates a state in which an electric signal is applied in the first and second electrodes 110 and 120 in the apparatus for analyzing the active material of the secondary battery 1 of FIG. 4.

Referring to FIG. 5, the electric signal is applied in the first and second electrodes 110 and 120 in the state in which the first and second active materials 210 and 220 and the electrolyte 230 are injected in the first and second through holes 141 and 142 and the electrolyte accommodation unit 251. Since the electric signal is applied in the first and second electrodes 110 and 120, an ultrasound wave may be generated in the piezoelectric layer 130. Accordingly, the ultrasound wave may be transmitted between the first active material 210 and the second electrode 120. Since the ultrasound wave is transmitted, a bonding property between the first active material 210 and the second electrode 120 may change. Accordingly, the bonding property between the first active material 210 and the second electrode 120 may be detected via the apparatus for analyzing the active material of the secondary battery 1 according to some example embodiments.

Meanwhile, a size of the first through hole 141 may vary. Accordingly, a volume and a state of the first active material 210 injected in the first through hole 141 may be set differently. Accordingly, at least one of a property of the first active material 210 when the first active material 210 is in a particle state, and a property of the first active material 210 when the first active material 210 is in a bulk state may be detected.

Figure 6A:
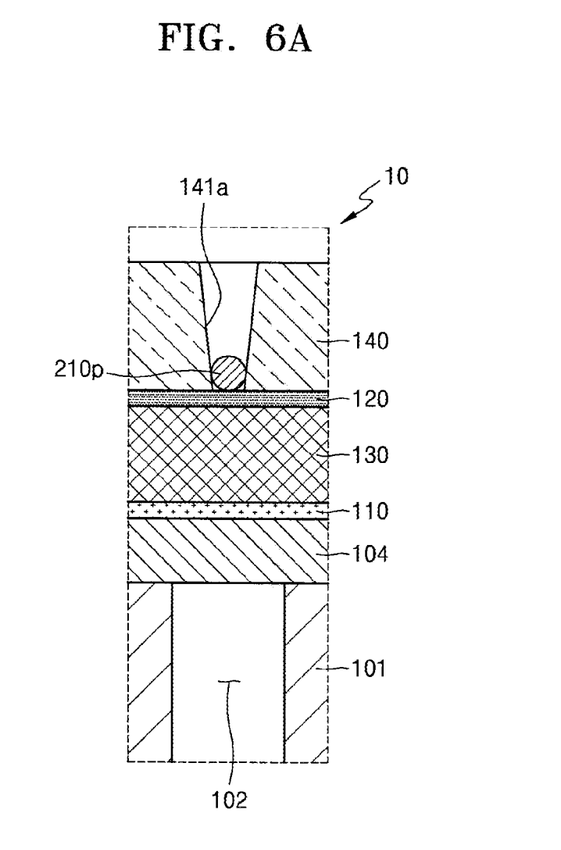
FIGS. 6A and 6B are views of various examples of a first active material which is injected in a first through hole.
Figure 6B:
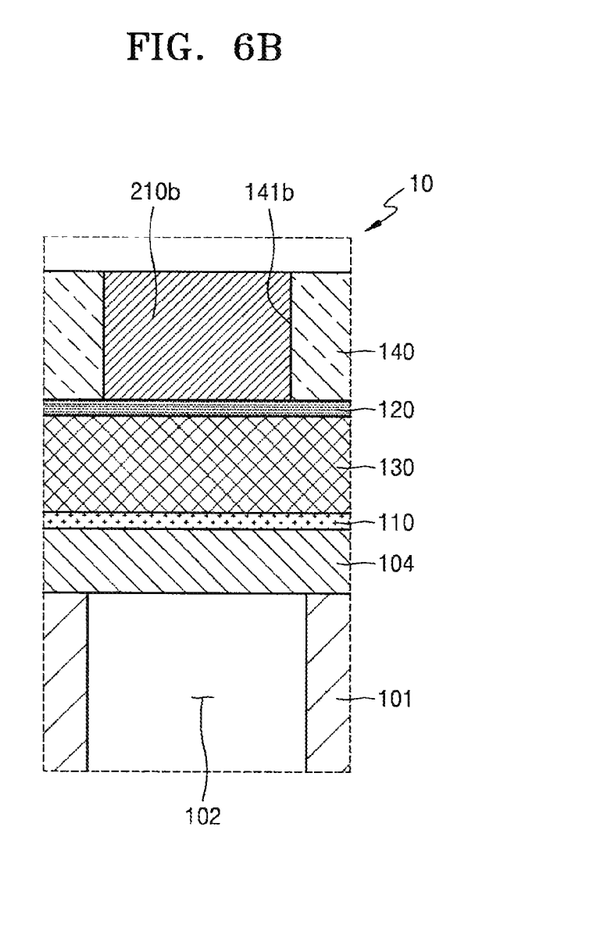

FIGS. 6A and 6B are views of various examples of the first active material 210 which is injected in the first through hole 141.

Referring to FIG. 6A, a first active material 210p may have a size of an active material particle unit. A diameter of the first active material 210p may be equal to or less than a few microns (μm). For example, the diameter of the first active material 210p may be about 8 μm. Here, a size of a first through hole 141a may correspond to the size of the first active material 210p. For example, the size (e.g., diameter) of the first through hole 141a may also be a few μm. Accordingly, a weight of the active material particle unit of the first active material 210p may be precisely detected and based on this, electrical and chemical properties of the particle unit of the first active material 210p may be detected.

Referring to FIG. 6B, a first active material 210b may have a size of a bulk unit in which a plurality of active material particles are included. The size (e.g., diameter) of the first active material 210b may be a few millimeters (mm). Here, in addition to the plurality of active material particles, the first active material 210b may include other materials, such as a binder, a coating film, and a conductive agent. Here, a size of a first through hole 141b may correspond to the size of the first active material 210b. For example, the size of the first through hole 141b may be a few mm. Accordingly, through a property of the first active material 210b in the bulk unit, a property of an electrode layer including the first active material 210b in a secondary battery may be detected.

Figure 7:
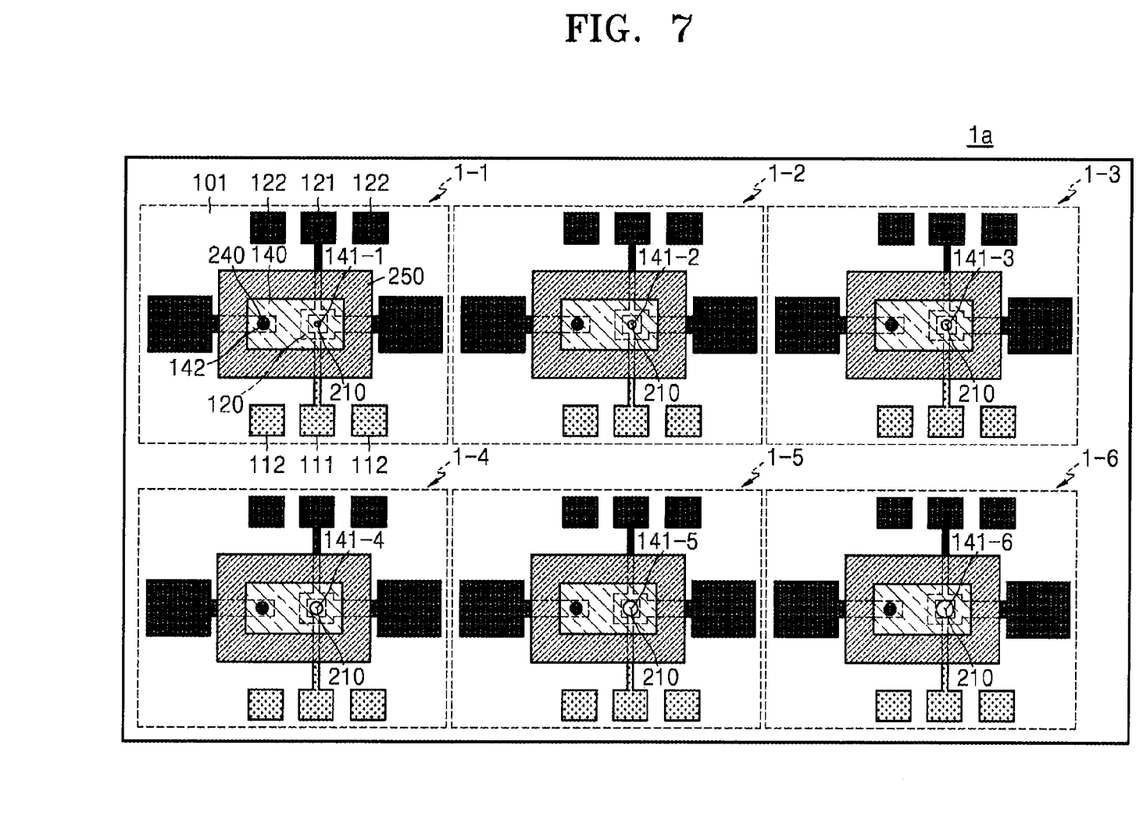
FIG. 7 is a plan view of an apparatus for analyzing an active material of a secondary battery according to some example embodiments.

FIG. 7 is a plan view of an apparatus for analyzing an active material of a secondary battery 1a according to some example embodiments.

Referring to FIG. 7, the apparatus for analyzing the active material of the secondary battery 1a may include a plurality of active material analyzing modules 1-1, 1-2, 1-3, 1-4, 1-5, and 1-6, with the apparatus for analyzing the active material of the secondary battery 1 described above as one battery analysis module.

The plurality of active material analyzing modules 1-1, 1-2, 1-3, 1-4, 1-5, and 1-6 are formed on the substrate 101. Each of the plurality of active material analyzing modules 1-1, 1-2, 1-3, 1-4, 1-5, or 1-6 may include the first electrode 110, the piezoelectric layer 130, the second electrode 120, the insulating layer 140, and the chamber layer 250. The first and second through holes 141 and 142 are formed on the insulating layer 140.

At least some of first through holes 141-1, 141-2, 141-3, 141-4, 141-5, and 141-6 of the plurality of active material analyzing modules 1-1, 1-2, 1-3, 1-4, 1-5, and 1-6 may have different sizes. For example, the first through hole 141-1 of the first active material analyzing module 1-1 and the first through hole 141-6 of the sixth active material analyzing module 1-6 may have different sizes. Accordingly, a weight of a particle unit of the first active material 210 and a weight of a bulk unit of the first active material 210 may be precisely detected at the same time. Accordingly, electrical and chemical properties of the first active material 210 may be easily detected, according to a change in the weight and state of the first active material 210.

In the apparatus for analyzing the active material of the secondary battery 1a according to some example embodiments, a plurality of battery analysis modules are formed on the substrate 101. The plurality of battery analysis modules may be easily formed by using semiconductor processes. Thus, the apparatus for analyzing the active material of the secondary battery 1a may be simply manufactured, and electric and chemical properties of the active material according to the change in the weight and state may be easily detected.

Figure 8:
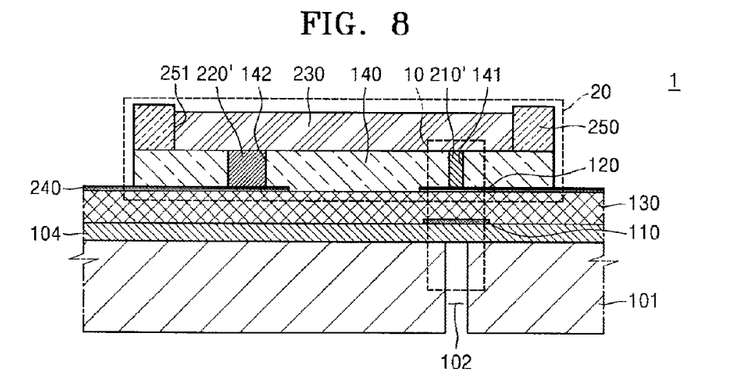
FIG. 8 illustrates another example of the state in which the first and second active materials and the electrolyte are injected in the first and second through holes and the electrolyte accommodation unit, in the apparatus for analyzing the active material of the secondary battery of FIG. 2.

In some example embodiments, the first active material 210 injected in the first through hole 141 is the positive active material. However, the first active material 210 is not limited thereto. For example, as illustrated in FIG. 8, a first active material 210' may be a negative active material and a second active material 220' may be a positive active material.

Figure 9:
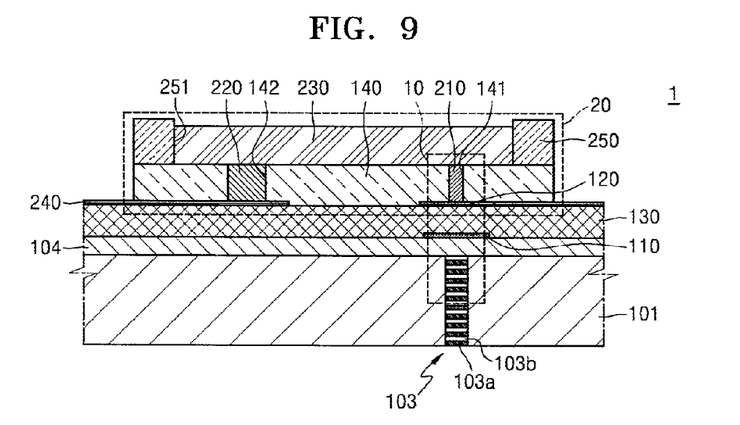
FIG. 9 is a cross-sectional view of an apparatus for analyzing an active material of a secondary battery according to some example embodiments.

Also, in some example embodiments, the film bulk acoustic resonator 10 including the cavity 102 in a region of the substrate 101, which overlaps the first through hole 141, is exemplified as the bulk acoustic resonator. However, the bulk acoustic resonator 10 is not limited thereto. As illustrated in FIG. 9, the bulk acoustic resonator 10 may be a solidly mounted resonator (SMR) including a reflective layer 103 in a region of the substrate 101, which overlaps the first through hole 141. The reflective layer 103 may have a structure in which a metal layer 103a and an insulating layer 103b are alternately stacked. In addition to this, any kind of bulk acoustic resonator which may be used for measuring weight by one of ordinary skill in the art may be used.

FIGS. 10A through 10D are views illustrating a method of analyzing an active material of a secondary battery according to some example embodiments.

Figure 10A:
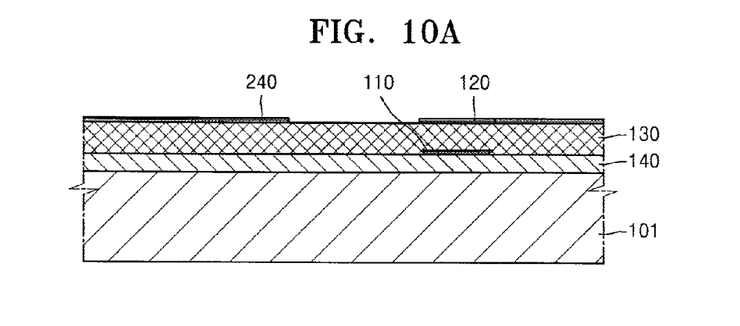
FIGS. 10A through 10D are views illustrating a method of analyzing an active material of a secondary battery according to some example embodiments.

Referring to FIG. 10A, the first electrode 110, the piezoelectric layer 130, and the second electrode 120 are sequentially formed on the substrate 101. When forming the second electrode 120, the third electrode 240 may be also formed to be apart from the second electrode 120.

The substrate 101 may be a silicon substrate. However, materials of the substrate 101 are not limited thereto and may vary. The insulating thin film 104 may be formed between the substrate 101 and the first electrode 110. The insulating thin film 104 may include silicon oxide.

The first electrode 110 may be a metal layer. The first electrode 110 may include any one selected from the metal materials consisting of Mo, Au, Cu, Pd, Ni, Ti, Cr, Fe, Co, Pt, and Ru, or any mixture thereof. The first electrode 110 may be formed on the substrate 101 by using a metal patterning method, such as etching and lifting off. The first electrode 110 may be formed to have a thickness of about 10 nm to about 1,000 nm.

The piezoelectric layer 130 is formed on the first electrode 110 and has a piezoelectric property. The piezoelectric layer 130 may include any one of AN, ZnO, and PZT or any mixture thereof. The piezoelectric layer 130 may be formed to have a thickness of about 10 nm to about 3,000 nm.

The second electrode 120 is formed on the piezoelectric layer 130 and may be a metal layer. The second electrode 120 may include any one selected from the metal materials consisting of Mo, Au, Cu, Pd, Ni, Ti, Cr, Fe, Co, Pt, and Ru, or any mixture thereof. The second electrode 120 may be formed on the substrate 101 by a metal patterning method, such as etching and lifting off. The second electrode 120 may be formed to have a thickness of about 10 nm to about 1,000 nm.

The third electrode 240 is formed on the piezoelectric layer 130 and may be a metal layer. However, locations of the third electrode 240 are not limited thereto and the third electrode 240 may be located at any place apart from the second electrode 120. The third electrode 240 may include any one selected from the metal materials consisting of Mo, Au, Cu, Pd, Ni, Ti, Cr, Fe, Co, Pt, and Ru, or any mixture thereof.

Figure 10B:
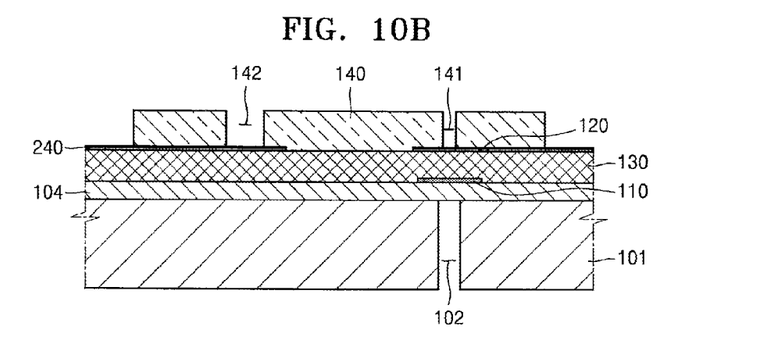

Referring to FIG. 10B, the insulating layer 140 is formed on the second and third electrodes 120 and 240 and the piezoelectric layer 130. The insulating layer 140 may be formed by using various methods, such as ALD, CVD, and evaporation.

To form the first through hole 141 exposing a portion of the second electrode 120 and the second through hole 142 exposing a portion of the third electrode 240 on the insulating layer 140, a portion of the insulating layer 140 may be removed. Methods of removing the portion of the insulating layer 140 may vary, and one example of the methods is etching.

The substrate 101 may include the cavity 102 in a portion of the region of the substrate 101, the region overlapping the first electrode 110. In some example embodiments, although it is not illustrated in FIG. 10B, the reflective layer 103 may be formed in the cavity 102.

Figure 10C:
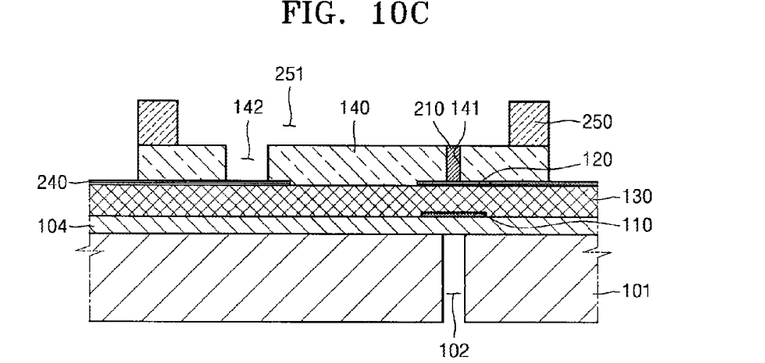

Referring to FIG. 10C, the first active material 210 is injected in the first through hole 141. After the first active material 210 is injected, a resonance frequency of the piezoelectric layer 130 is measured. A weight of the first active material 210 is detected by comparing the measured resonance frequency and a resonance frequency of the piezoelectric layer 130 before the first active material 210 is injected.

Before or after the first active material 210 is injected, the chamber layer 250 is formed on the insulating layer 140. The electrolyte accommodation unit 251 is defined above the first and second through holes 141 and 142 by the chamber layer 250.

Figure 10D:
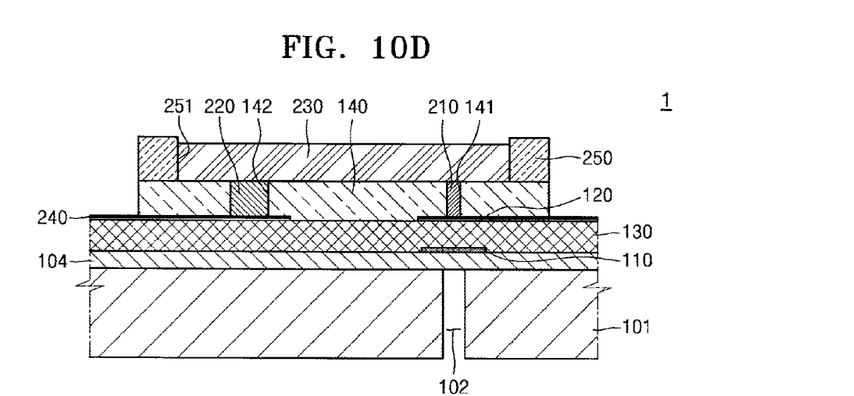

Referring to FIG. 10D, the second active material 220 which has a different charge and discharge potential to that of the first active material 210 is injected in the second through hole 142, and the electrolyte 230 is injected in the electrolyte accommodation unit 251.

As shown above, in the state in which the first and second active materials 210 and 220 and the electrolyte 230 are injected in the first and second through holes 141 and 142 and the electrolyte accommodation unit 251, electrical and chemical properties of the first active material 210 are detected by using the second and third electrodes 120 and 240. Accordingly, the electrical and chemical properties of the first active material 210 per unit weight may be detected. Also, when the bulk of the first active material 210 is known, the electrical and chemical properties of the first active material 210 per density may be detected.

As described above, according to some example embodiments, the weight of the active material may be measured by using the bulk acoustic resonator and the electrical and chemical properties may be directly detected without moving the active material and, thus, the electrical and chemical properties of the active material per density may be precisely measured.

It should be understood that the example embodiments described herein should be considered in a descriptive sense only and not for purposes of limitation. Descriptions of features or aspects within each embodiment should typically be considered as available for other similar features or aspects in other embodiments.

While some example embodiments of the present inventive concept have been described with reference to the figures, it will be understood by those of ordinary skill in the art that various changes in form and details may be made herein without departing from the spirit and scope of the present inventive concept as defined by the following claims.

What is claimed is:

1. An apparatus for analyzing an active material of a secondary battery, the apparatus comprising:
   a first electrode;
   a piezoelectric layer on the first electrode;
   a second electrode on the piezoelectric layer, configured to provide a voltage having a polarity opposite to a polarity of the first electrode;
   a third electrode spaced apart from the second electrode; and
   an insulating layer on the second electrode, the insulating layer comprising a first through hole exposing a portion of the second electrode and a second through hole not overlapping the second electrode and spaced apart from the first through hole,
   wherein the second through hole exposes a portion of the third electrode.

2. The apparatus of claim 1, wherein a first active material is injected in the first through hole, and
   wherein a weight of the first active material accommodated in the first through hole is detected based on a resonance frequency generated in the piezoelectric layer.

3. The apparatus of claim 2, wherein a second active material, having a different charge and discharge potential from the first active material, is injected in the second through hole.

4. The apparatus of claim 1, wherein a chamber layer, which encloses the first and second through holes and in which an electrolyte is accommodated, is above the insulating layer.

5. The apparatus of claim 1, further comprising:
   a substrate below the first electrode.

6. The apparatus of claim 5, wherein the substrate comprises:
   a cavity in at least a portion of a region of the substrate;
   wherein the region overlaps the first electrode.

7. The apparatus of claim 5, wherein the substrate comprises:
   a reflective layer in at least a portion of a region of the substrate;
   wherein the region overlaps the first electrode.

8. A method of analyzing an active material of a secondary battery, the method comprising:
   disposing a first active material in a first through hole of a bulk acoustic resonator, in which a first electrode, a piezoelectric layer, a second electrode, and an insulating layer are sequentially stacked, wherein the first through hole is in the insulating layer to expose a portion of the second electrode;
   measuring a resonance frequency of the bulk acoustic resonator by applying an electric signal to the first and second electrodes of the bulk acoustic resonator; and
   measuring a weight of the first active material in the first through hole, based on the measured resonance frequency,
   wherein the first active material is a positive active material or a negative active material.

9. The method of claim 8, further comprising:
   disposing a second active material apart from the first active material; and
   disposing an electrolyte to contact the first and second active materials.

10. The method of claim 9, further comprising:
    detecting electrical and chemical properties of the first active material per unit weight.

11. The method of claim 9, wherein the second active material has a different charge and discharge potential from the first active material.

12. The method of claim 9, further comprising:
    generating an ultrasound wave by applying an electric signal to the first and second electrodes; and
    detecting a bonding property between the second electrode and the first active material by using the generated ultrasound wave.

13. An apparatus for analyzing an active material of a secondary battery, the apparatus comprising:
    a first electrode;
    a piezoelectric layer on the first electrode;
    a second electrode on the piezoelectric layer, the second electrode being configured to provide a voltage having a polarity that is opposite to a polarity of the first electrode;
    an insulating layer on the second electrode and comprising a first through hole exposing a portion of the second electrode, and
    a chamber layer on the insulating layer, the chamber layer defining an electrolyte accommodating unit in which an electrolyte is accommodated,
    wherein a size of the first through hole is smaller than a size of the piezoelectric layer, and
    a portion of the electrolyte accommodating unit overlaps the first through hole.

* * * * *